US012533515B2

(12) United States Patent
Cevette et al.

(10) Patent No.: US 12,533,515 B2
(45) Date of Patent: Jan. 27, 2026

(54) COCHLEAR STIMULATION SYSTEM WITH SURROUND SOUND AND NOISE CANCELLATION

(71) Applicant: Mayo Foundation for Medical Education and Research, Rochester, MN (US)

(72) Inventors: Michael J. Cevette, Cave Creek, AZ (US); Jan Stepanek, Scottsdale, AZ (US); Gaurav N. Pradhan, Fountain Hills, AZ (US); Kenneth H. Brookler, Norwalk, CT (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 352 days.

(21) Appl. No.: 16/083,656

(22) PCT Filed: Mar. 9, 2017

(86) PCT No.: PCT/US2017/021579
§ 371 (c)(1),
(2) Date: Sep. 10, 2018

(87) PCT Pub. No.: WO2017/156276
PCT Pub. Date: Sep. 14, 2017

(65) Prior Publication Data

US 2019/0070414 A1 Mar. 7, 2019

Related U.S. Application Data

(60) Provisional application No. 62/306,836, filed on Mar. 11, 2016.

(51) Int. Cl.

| | |
|---|---|
| *A61N 1/36* | (2006.01) |
| *A61N 1/05* | (2006.01) |
| *H04R 25/00* | (2006.01) |

(52) U.S. Cl.
CPC ....... *A61N 1/36038* (2017.08); *A61N 1/0541* (2013.01); *A61N 1/36* (2013.01);
(Continued)

(58) Field of Classification Search
CPC ..................................................... A61N 1/0541
See application file for complete search history.

(56) References Cited

U.S. PATENT DOCUMENTS 3,393,279 A 7/1968 Flanagan
3,586,791 A 6/1971 Puharich et al.
(Continued)

FOREIGN PATENT DOCUMENTS

CN 101491116 A 7/2009
CN 102984637 A 3/2013
(Continued)

OTHER PUBLICATIONS

International Preliminary Report on Patentability issued in PCT/US2017/021579, mailed Sep. 20, 2018, 6 pages.
(Continued)

*Primary Examiner* — Jennifer Pitrak McDonald
*Assistant Examiner* — Jennifer L Ghand

(57) ABSTRACT

A cochlear and nerve stimulation system comprises a signal input to receive an audio input signal, a multiple channel microphone input to receive multiple channel ambient noise signals, and a multiple channel cochlear converter coupled to the signal input to produce multiple channel surround sound cochlear and nerve stimulation signals based on the audio input signal. The stimulation signals include one or both of interaural level differences and interaural time differences. A sound canceling processor is coupled between the microphone input and the cochlear converter to produce multiple channel sound canceling signals based on the ambient noise signals. Multiple channel cochlear and nerve
(Continued)

stimulation electrodes are configured for attachment to a user and coupled to receive the multiple channel surround sound cochlear stimulation signals.

20 Claims, 3 Drawing Sheets

(52) U.S. Cl.
CPC ......... *H04R 25/505* (2013.01); *H04R 25/552* (2013.01); *H04R 2225/67* (2013.01); *H04R 2430/01* (2013.01); *H04S 2420/01* (2013.01)

(56) References Cited

U.S. PATENT DOCUMENTS

| | | | | |
|---|---|---|---|---|
| 3,766,331 | A | 10/1973 | Zink | |
| 5,824,022 | A * | 10/1998 | Zilberman | A61N 1/36038 607/57 |
| 8,126,565 | B1 | 2/2012 | Litvak et al. | |
| 8,417,348 | B2 | 4/2013 | Schleich | |
| 8,948,877 | B2 | 2/2015 | Schleich et al. | |
| 9,071,896 | B2 | 6/2015 | Goodman et al. | |
| 2005/0078833 | A1 | 4/2005 | Hess et al. | |
| 2005/0111683 | A1* | 5/2005 | Chabries | H04R 25/356 381/317 |
| 2005/0135643 | A1* | 6/2005 | Lee | H04S 7/301 381/309 |
| 2005/0251225 | A1* | 11/2005 | Faltys | A61N 1/36038 607/57 |
| 2006/0045294 | A1 | 3/2006 | Smyth | |
| 2007/0016267 | A1* | 1/2007 | Griffin | A61N 1/36038 607/57 |
| 2009/0046874 | A1 | 2/2009 | Doman | |
| 2009/0116657 | A1* | 5/2009 | Edwards | H04R 25/552 381/60 |
| 2009/0143848 | A1* | 6/2009 | Greenberg | A61N 1/0541 607/137 |
| 2009/0304203 | A1* | 12/2009 | Haykin | G10L 21/02 381/94.1 |
| 2009/0304210 | A1* | 12/2009 | Weisman | H04R 1/46 381/151 |
| 2011/0188662 | A1 | 8/2011 | Jensen et al. | |
| 2012/0232616 | A1 | 9/2012 | Van Baelen et al. | |
| 2014/0316771 | A1 | 10/2014 | Short et al. | |
| 2015/0133716 | A1 | 5/2015 | Suhami et al. | |
| 2015/0208956 | A1 | 7/2015 | Schmitt | |
| 2015/0306388 | A1 | 10/2015 | Nogueira et al. | |
| 2015/0367132 | A1 | 12/2015 | Milczynski et al. | |
| 2016/0112811 | A1* | 4/2016 | Jensen | G10L 21/0232 381/17 |
| 2017/0048627 | A1 | 2/2017 | Fitz | |
| 2018/0041848 | A1* | 2/2018 | Nielsen | H04S 7/30 |
| 2019/0070414 | A1* | 3/2019 | Cevette | H04R 25/505 |

FOREIGN PATENT DOCUMENTS

| | | | |
|---|---|---|---|
| CN | 104703108 | A | 6/2015 |
| CN | 104936117 | A | 9/2015 |
| DE | 10040660 | A1 | 2/2001 |
| EP | 0830802 | A1 | 3/1998 |
| EP | 2806661 | A1 | 11/2014 |
| JP | 2002-509761 | A | 4/2002 |
| JP | 2009-049844 | A | 3/2009 |
| JP | 2009-542038 | A | 11/2009 |
| JP | 2014-508611 | A | 4/2014 |

OTHER PUBLICATIONS

International Search Report and Written Opinion issued in PCT/US2017/021579, mailed Jun. 7, 2017, 9 pages.
Extended European Search Report issued in EP Application No. 17764100.8, mailed Oct. 11, 2019, 9 pages.

* cited by examiner

COCHLEAR STIMULATION SYSTEM WITH SURROUND SOUND AND NOISE CANCELLATION

CROSS-REFERENCE TO RELATED APPLICATION

This application is a national phase application of PCT Application No. PCT/US2017/021579, internationally filed on Mar. 9, 2017, which claims the benefit of U.S. Provisional Application No. 62/306,836, filed on Mar. 11, 2016, both of which are herein incorporated by reference in their entireties for all purposes.

FIELD OF THE INVENTION

The invention relates generally to cochlear stimulation devices and methods that electrically stimulate the sensation of hearing, for example in persons having hearing disabilities.

BACKGROUND

Cochlear stimulation systems and methods for externally electrically stimulating the sensations of hearing are generally known and disclosed, for example, in the Zink U.S. Pat. No. 3,766,331, Litvak U.S. Pat. No. 8,126,565, Schleich U.S. Pat. No. 8,417,348, Schleich U.S. Pat. No. 8,948,877 and Goodman U.S. Pat. No. 9,071,896, all of which are incorporated herein by reference for all purposes. These systems and methods use electrodes positioned on the user's head to transmit electrical signals that stimulate the cochlea and auditory nerve to provide the sensation of hearing. There remains, however, a continuing need for improved electrically stimulated sound systems.

SUMMARY

A cochlear stimulation system in accordance with embodiments of the invention comprises a signal input to receive an audio input signal and a multiple channel cochlear converter coupled to the signal input. The cochlear converter produces multiple channel surround sound cochlear stimulation signals based on the audio input signal. Other embodiments further include multiple channel cochlear stimulation electrodes. Each of the electrodes is configured for attachment to a user and coupled to receive one of the multiple channel surround sound cochlear stimulation signals. Yet other embodiments include a microphone input for receiving ambient noise signals and a sound canceling processor coupled between the microphone input and the cochlear converter. The sound canceling processor produces sound canceling signals based on the ambient noise signals, and wherein the cochlear converter produces the surround sound cochlear stimulation signals based on the sound canceling signals. In embodiments, the cochlear converter produces multiple channel stimulation signals having interaural level differences and/or interaural time differences.

DESCRIPTION OF THE INVENTION

Figure 1:
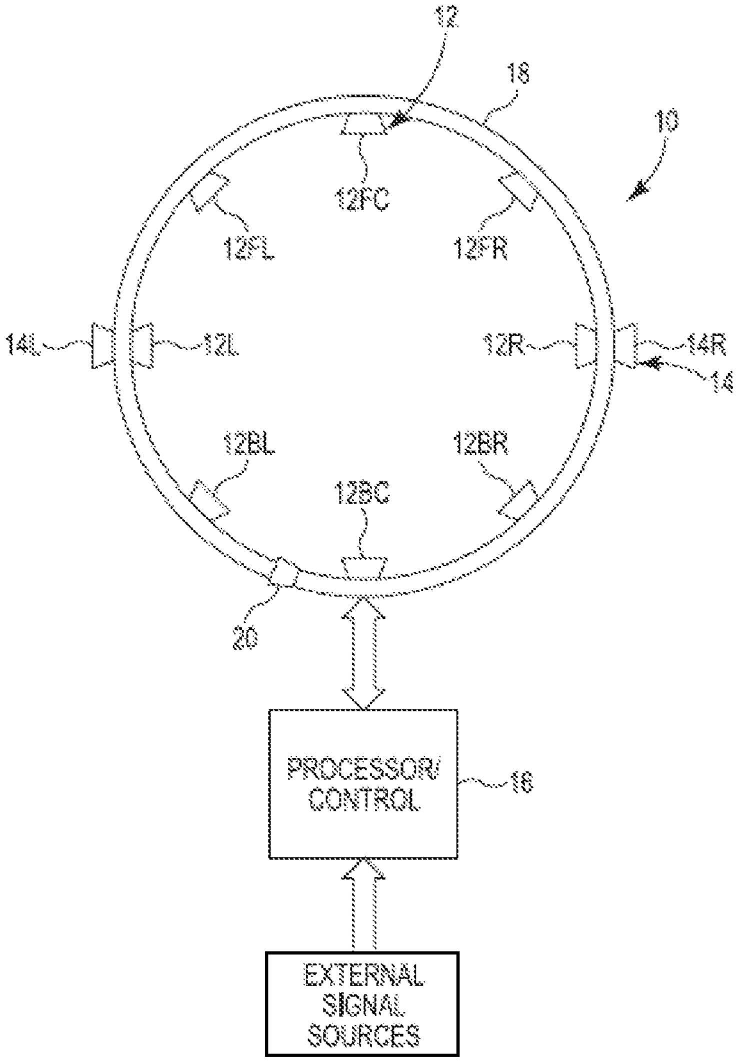
FIG. 1 is a diagrammatic illustration of a cochlear stimulation system in accordance with embodiments of the invention.

FIG. 1 illustrates a cochlear and auditory nerve stimulation system 10 having surround sound and/or noise cancellation capabilities in accordance with embodiments of the invention. As shown, system 10 includes multiple channel stimulation electrodes 12, multiple channel microphones 14, and a processor/control 16. The illustrated embodiment includes front center, front left, front right, left, right, back center, back left and back right channel electrodes 12FC, 12FL, 12FR, 12L, 12R, 12BC, 12BL and 12 BR, respectively. Other embodiments (not shown) have more or fewer electrodes 12. Left and right channel microphones 14L and 14R, respectively, are shown in FIG. 1, although other embodiments (not shown) have more or fewer microphones 14. Electrodes 12 and microphones 14 are configured to be attached to or worn at spaced apart locations around the user's head or neck. For example, in the illustrated embodiment, the electrodes 12 and microphones 14 are attached at spaced-apart locations to a structure such as a strap 18 that can be attached to the user's head or neck. A coupler, such as buckle 20 on the strap 18, can facilitate mounting the strap to the user.

Processor/control 16 has an input that can be coupled to a source of external audio signals (not shown). System 10 can, for example, be configured to interface to mobile devices, DVD players and other sources of audio content such as cable, satellite and television broadcasts and theaters. In response to the audio signals, processor/control 16 generates multiple channel surround sound electrode drive signals that are coupled to associated channel stimulation electrodes 12. The application of the surround sound drive signals to the user causes the sensation of hearing with the enriched reproduction and spatial qualities of surround sound (e.g., sequenced to have directionality and laterality). Based on timing and intensity cues, sound can be moved around the user's head. In embodiments, processor/control 16 also has an input coupled to a source, such as microphones 14, of ambient noise signals. In response to the ambient noise signals, the processor/control 16 causes the surround sound drive signals to be produced in a manner that causes global and/or directional cancellation of the ambient noise, thereby enabling enhanced hearing of the desired surround sound audio.

Figure 2:
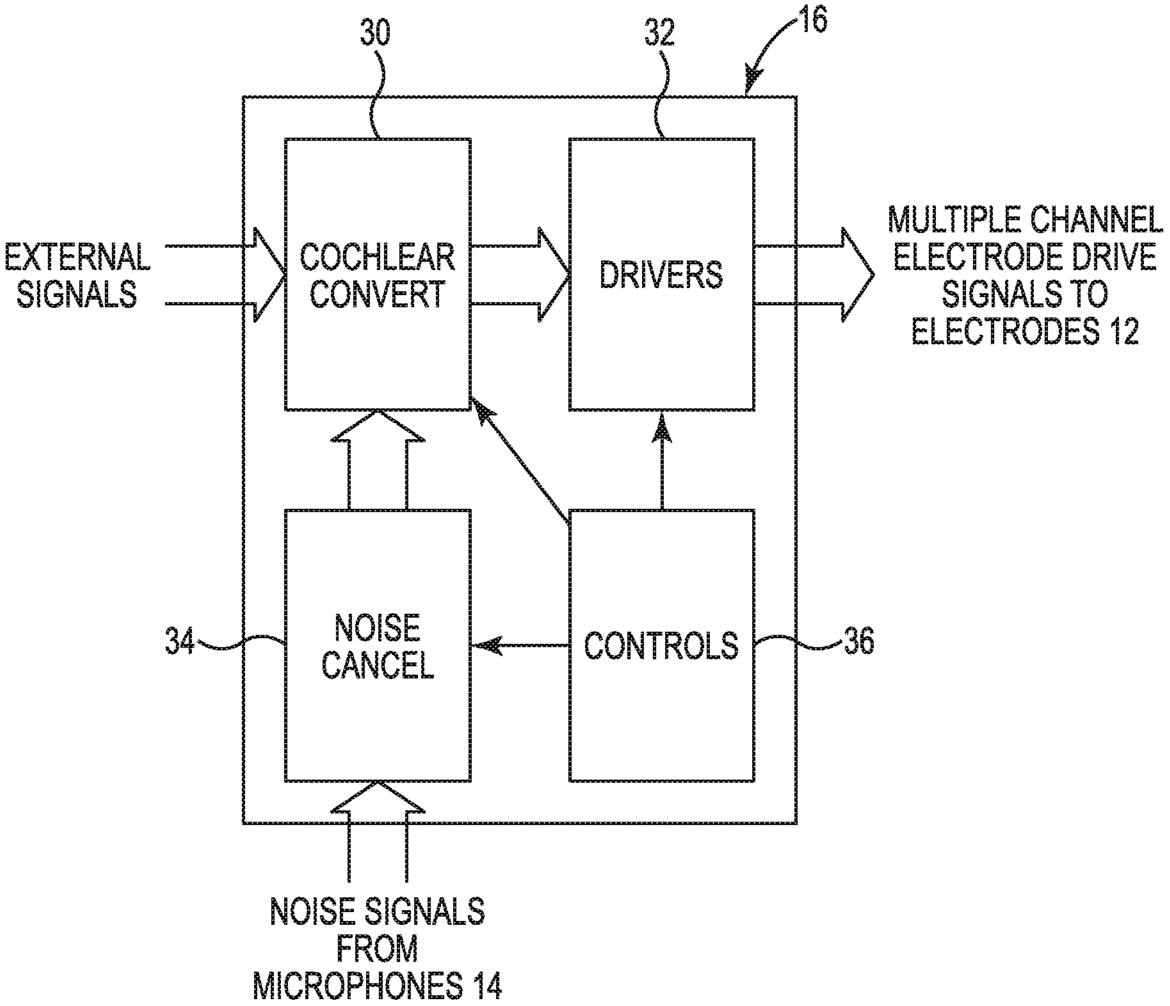
FIG. 2 is a block diagram of embodiments of the processor/control shown in FIG. 1.

FIG. 2 is a block diagram of a processor/control 16 in accordance with embodiments of the invention. The illustrated embodiment includes a cochlear converter 30, drivers 32, noise canceler 34 and controls 36. In embodiments, components of processor/control 16 such as cochlear converter 30 and/or noise canceler 34 can be implemented, for example, as a programmed processor (with associated memory), digital signal processor and/or discrete circuit components (not illustrated). Cochlear converter 30 receives, as an input, multiple channel surround sound-formatted audio signals corresponding to each of the multiple channel electrodes 12 (e.g., front center, front left, front right, right, left, back, back left, and back right signals in the illustrated embodiment). Any of a range of known surround sound technologies and formats can be used in system 10. The converter 30 converts those inputted audio signals to corresponding multiple channel cochlear and nerve simulation signals having characteristics or signal parameters that can produce, in the user, the sensation of hearing with the audio content of the inputted audio signals. By way of example, cochlear converter 30 can use structures and/or methods of the types disclosed in the U.S. patents identified in the Background section above to provide this conversion functionality, or other known or otherwise conventional structures and/or methods. Briefly, and by way of example, cochlear converter 30 can produce low RF frequency (e.g., about 60 kHz) signals that are modulated by audio frequencies corresponding to the audio content of the associated channels.

In some embodiments, processor/control 16 receives multiple channel audio signals from the signal source, and cochlear converter 30 converts each of those input signals to the associated stimulation signals. In other embodiments the processor/control 16 receives a single channel audio signal, or a signal having fewer channels than electrodes 12. Such embodiments can include a surround sound generator or synthesizer (not shown) that generates signals corresponding to each channel of the system 10 before those individual channel signals are processed by the cochlear converter 30.

In embodiments, the channel stimulation signals produced by the cochlear converter 30 are applied to drivers 32 before being applied to the electrodes 12. Drivers 32 can, for example, include transformers or other components that convert or change the voltage and/or current levels of the stimulation signals to levels capable of providing the efficacious hearing results when the stimulation signals are applied to the user.

Noise canceler 34 receives signals representative of ambient noise in the vicinity of the user. In response to the ambient noise signals, the noise canceler 34 produces signals that, after being coupled to cochlear converter 30, will cause the cochlear converter to produce the stimulation signals in such a manner as to effectively cancel out the ambient noise. Known or otherwise conventional noise cancellation methodologies can be used for this purpose. For example, the cochlear converter 30 can produce stimulation signals having components with the same frequency and content as the ambient noise signals, but 180° out of phase with the ambient noise signals. In embodiments, the noise canceler 34 can produce control signals characteristic of the ambient noise signals. In these embodiments, the cochlear converter 30 can use the control signals to control the generation of the channel stimulation signals. In other embodiments, the noise canceler 34 can produce audio signals that are summed with the audio signals applied to the cochlear converter 30 to effectively cancel the ambient noise before the audio signals are processed by the cochlear converter.

In embodiments, the noise canceler 34 functions globally by producing the same noise cancellation effects on all the channel stimulation signals. In such embodiments, for example, the ambient noise signals can be provided by either of microphones 14R and 14L. In other embodiments, the noise canceler 34 uses multiple channel ambient noise signals representative of ambient noise from different directions provided by each of several different microphones such as 14R and 14L, and causes the cochlear converter 30 to produce channel stimulation signals providing directional-specific noise cancellation. For example, the noise cancellation effects provided by the stimulation signal applied to electrodes 12FL, 12L and/or 12BL can be based upon the ambient noise signals provided by microphone 14L, and the stimulation signal applied to electrodes 12FR, 12R and/or 12BR can be based upon the ambient noise signals provided by microphone 14R. Such directional or multi-channel noise cancellation can, for example, be particularly efficacious for users having single-sided hearing loss.

Controls 36 can be coupled to cochlear converter 30, drivers 32 and/or noise canceler 34 and actuated by the user to control the system 10. By way of example, controls 36 can control the volume of the hearing provided by the stimulation signals, and the balance or relative volumes between the electrodes 12. In other embodiments, the frequency content or the tone of the hearing can be controlled by controls 36.

Other embodiments, alternatively or additionally to those described above, include an array of multiple electrodes (which can be incorporated into a contact) around the head. The linear accelerators of the inner ear, namely the otoliths, coupled with the angular accelerator of the semicircular canals have carrier frequencies ranging from approximately 10 kHz to over 60 kHz. A corresponding frequency of stimulation, which can be applied to one of the electrodes, may produce a sensation of pitch. Stimulation of the semicircular canals (e.g., by a signal applied to a second set of the electrodes), may produce a sensation of yaw and roll. Yet additional electrodes in the headband can stimulate to produce vector stimulation. Additional electrodes can have a 60 kHz carrier frequency for stimulation of hearing and binaural. Depending upon the surround sound output of a particular production, yet additional 60 kHz carrier frequency electrodes can be added (e.g., to the headband) to produce the surround sound effect.

Figure 3:
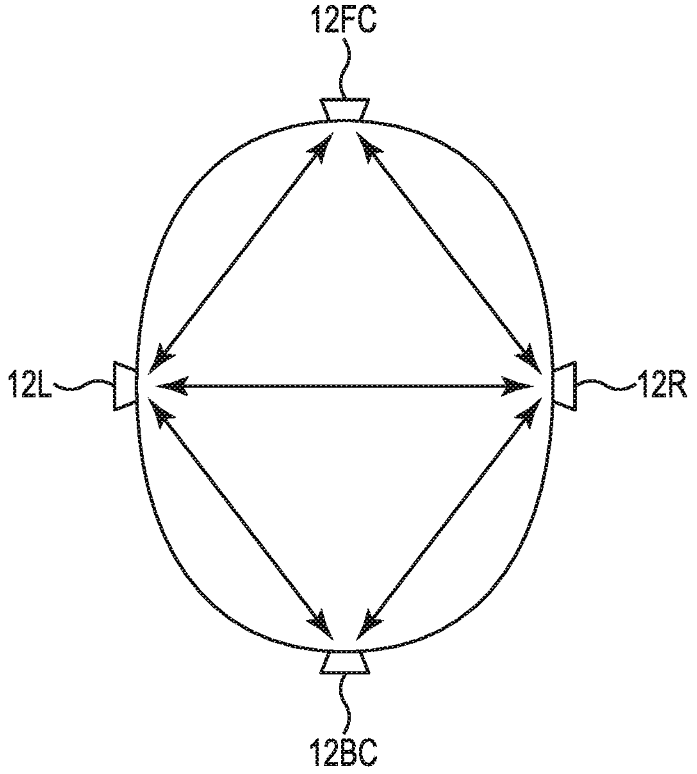
FIG. 3 is diagrammatic illustration of the use of the system to stimulate sound in different directions to provide perceptions of lateralization.

FIG. 3 is a diagrammatic illustration of front center, back center, left and right channel electrodes 12FC, 12BC, 12L and 12R, respectively, attached to a user, and lines illustrating a number of different directions of stimulation by those channel electrodes to provide the user with a perception of lateralization or different spatial locations of sound. Interaural time differences ("ITDs;" differences in time between stimulation provided by different channel electrodes) and/or interaural level differences ("ILDs;" differences in level or amplitude between stimulation provided by different channel electrodes) can be used to manipulate the perception of the location and directionality of sound (i.e., lateralization) within the head of a user. ILDs can be particularly useful to reflect the spatial locations of sounds with higher frequencies through the use of differences in sound pressure level (SPL) arriving at each ear. ITDs are particularly useful to provide the perception of lateralization at lower frequencies by timing differences for sound reaching each ear. In embodiments, ILDs and/or ITDs are provided between channel electrodes by processor/control 16 to manipulate the perception of the location of the sound (e.g., in front of, behind, left and/or right of the user). By varying the ILDs and/or ITDs, the perception of dynamically varying locations of the sound can also be provided.

Although the invention has been described with reference to preferred embodiments, those of skill in the art will recognize that changes can be made in form and detail without departing from the spirit and scope of the invention.

The invention claimed is:

1. A system for electrically stimulating a sensation of hearing, comprising:

a signal input to receive an audio input signal which is a multiple channel surround sound-formatted signal representative of audio content from an external source spaced apart from the user;

a multiple channel converter coupled to the signal input to produce multiple channel surround sound stimulation signals based on the audio input signal;

a multiple channel microphone input for receiving multiple channel ambient noise signals representative of ambient audio content at a vicinity of the user;

a sound canceling processor coupled between the microphone input and the converter to produce multiple channel sound canceling signals based on the multiple channel ambient noise signals; and multiple channel stimulation electrodes configured to be positioned at spaced apart locations on an exterior surface of a head or neck of the user outside of the ear canal of the user and coupled to the multiple channel converter to receive one of the multiple channel surround sound stimulation signals; and wherein the converter produces the surround sound stimulation signals based on the multiple channel sound canceling signals, wherein the surround sound stimulation signals are electrical signals configured to electrically stimulate a cochlea of the user when applied to the head or neck of the user via the multiple channel stimulation electrodes and provide the sensation of hearing including lateralization.

2. The system of claim 1, wherein:

the multiple channel converter produces at least front, left and right stimulation signals; and the multiple channel stimulation electrodes include at least front, left and right stimulation electrodes coupled to receive the front, left and right stimulation signals, respectively.

3. The system of claim/wherein:

the converter produces the front stimulation signals having one or more of front center, front left and front right stimulation signals; and the front stimulation electrode includes one or more of front center, front left and front right electrodes.

4. The system of claim 3 wherein:

the converter produces the stimulation signals having one or more of back left and back right stimulation signals; and the stimulation electrodes include one or more of back left and back right electrodes.

5. The system of claim 1 and further including a mounting device configured to mount the stimulation electrodes to the user.

6. The system of claim 1 wherein the sound canceling processor is configured to produce the sound canceling signals, and wherein the sound canceling signals are audio signals configured to be summed with the audio input signal.

7. The system of claim 1 wherein the sound canceling processor produces the sound canceling signals, and wherein the sound canceling signals are control signals configured to control the generation of the stimulation signals.

8. The system of claim 1 and further including controls to control one or more of the volume of hearing provided by the stimulation signals, relative volumes, frequency content or tone.

9. The system of claim 1 and further including drivers, comprising transformers, coupling the stimulation electrodes to the converter.

10. The system of claim 1 wherein the converter produces multiple channel stimulation signals having interaural level differences.

11. The system of claim 10 wherein the converter produces multiple channel stimulation signals having interaural time differences.

12. The system of claim 11 wherein the converter produces multiple channel stimulation signals having changing interaural level and time differences.

13. The system of claim 1 wherein the converter produces multiple channel stimulation signals having interaural time differences.

14. The system of claim 1, and further including multiple channel microphones, each of the microphones configured for attachment to the user and coupled to the multiple channel microphone input.

15. The system of claim 14 and further including a mounting device configured to mount the stimulation electrodes and multiple channel microphones to a user.

16. The system of claim 1 and further including the external source, wherein the external source is coupled to the signal input, and is not worn by the user.

17. The system of claim 1, wherein the multiple channel stimulation electrodes comprise at least:

a left electrode configured for attachment to the exterior surface on a left side of the head or neck of the user;

a right electrode configured for attachment to the exterior surface on a right side of the head or neck of the user; and a front center electrode configured for attachment to the exterior surface on a front center side of the head or neck of the user, and/or a back center electrode configured for attachment to the exterior surface on a back center side of the head or neck of the user.

18. A system for stimulating the sensation of hearing in a user, comprising:

a signal input to receive an audio input signal representative of audio content from an external source spaced apart from the user;

multiple channel microphones to produce multiple channel ambient noise signals representative of ambient audio content at a vicinity of the user;

multiple channel stimulation electrodes configured to be attached to an exterior surface of a head or neck of the user at spaced apart locations around the user's head or neck and outside of ear canals of the user;

a multiple channel converter coupled to the multiple channel stimulation electrodes and to the signal input to produce multiple channel surround sound stimulation signals based on the audio input signal, wherein the stimulation signals include one or both of interaural level differences and interaural time differences, and wherein the surround sound stimulation signals are electrical signals configured to electrically stimulate a cochlea of the user when applied to the user via the multiple channel stimulation electrodes and provide sensations of hearing including lateralization; and a sound canceling processor coupled between the microphone input and the converter to produce multiple channel sound canceling signals based on the ambient noise signals, wherein the converter produces the surround sound stimulation signals based on the sound canceling signals.

19. The system of claim 18 and further including the external source, wherein the external source is coupled to the signal input, and is not worn by the user.

20. The system of claim 18, wherein the multiple channel stimulation electrodes comprise at least:

a left electrode configured for attachment to the exterior surface on a left side of the head or neck of the user;

a right electrode configured for attachment to the exterior surface on a right side of the head or neck of the user; and a front center electrode configured for attachment to the exterior surface on a front center side of the head or neck of the user, and/or a back center electrode configured for attachment to the exterior surface on a back center side of the head or neck of the user.

* * * * *